United States Patent [19]

Walling et al.

[11] Patent Number: 5,508,171

[45] Date of Patent: Apr. 16, 1996

[54] ASSAY METHOD WITH ENZYME ELECTRODE SYSTEM

[75] Inventors: P. Douglas Walling, Indianapolis; Joseph E. Bateson, Carmel; Lance S. Kuhn, Fishers; M. Luann Ochs, Fishers; Kent M. Kost, Fishers; Martin T. Gerber, Carmel, all of Ind.; Klaus H. Pollmann, Neulussheim, Germany; Chi-Neng A. Han, Philadelphia, Pa.

[73] Assignee: Boehringer Mannheim Corporation, Indianapolis, Ind.

[21] Appl. No.: 198,407

[22] Filed: Feb. 22, 1994

Related U.S. Application Data

[63] Continuation-in-part of Ser. No. 627,667, Dec. 14, 1990, Pat. No. 5,288,636, which is a continuation-in-part of Ser. No. 451,671, Dec. 15, 1989, abandoned.

[51] Int. Cl.$^6$ .............................. C12Q 1/26; C12Q 1/54
[52] U.S. Cl. ...................... 205/777.5; 435/25; 435/817; 205/782
[58] Field of Search .................................. 435/4, 14, 25, 435/288, 291, 817; 204/153.12, 153.17, 403, 415

[56] References Cited

U.S. PATENT DOCUMENTS

| | | | |
|---|---|---|---|
| 4,224,125 | 9/1980 | Nakamura et al. | 204/195 B |
| 4,543,326 | 9/1985 | Miyashita et al. | 435/15 |
| 4,758,323 | 7/1988 | Davis et al. | 204/403 |
| 4,810,633 | 3/1989 | Bauer et al. | 435/25 |
| 4,820,399 | 4/1989 | Senda et al. | 204/403 |
| 4,830,959 | 5/1989 | McNeil et al. | 436/7 |
| 4,894,137 | 1/1990 | Takizawa et al. | 204/403 |
| 4,897,173 | 1/1990 | Nankai et al. | 204/403 |
| 4,959,305 | 9/1990 | Woodrum | 435/7 |

FOREIGN PATENT DOCUMENTS

| | | | |
|---|---|---|---|
| 0080304 | 6/1983 | European Pat. Off. | C12N 9/96 |
| 0127958 | 12/1984 | European Pat. Off. | G01N 33/48 |
| 0136362A1 | 4/1985 | European Pat. Off. | G01N 27/30 |
| 0206218A2 | 12/1986 | European Pat. Off. | G01N 27/30 |
| 0230472 | 8/1987 | European Pat. Off. | G01N 27/30 |
| 0359831A1 | 3/1990 | European Pat. Off. | G01N 27/28 |
| 0400918A1 | 12/1990 | European Pat. Off. | G01N 27/30 |
| 60-173458 | 9/1985 | Japan | G01N 27/46 |
| 60-173457 | 9/1985 | Japan | G01N 27/46 |
| 60-173459 | 9/1985 | Japan | G01N 27/46 |
| 61-91558 | 5/1986 | Japan | G01N 27/30 |
| 61-90050 | 5/1986 | Japan | G01N 27/30 |
| 63-58149 | 3/1988 | Japan | G01N 27/46 |
| 63-128252 | 5/1988 | Japan | G01N 27/46 |
| 63-139246 | 6/1988 | Japan | G01N 27/30 |
| 63-317757 | 12/1988 | Japan | G01N 27/30 |
| 63-317758 | 12/1988 | Japan | G01N 27/30 |
| 64-23153 | 1/1989 | Japan | G01N 27/30 |
| 1-134244 | 5/1989 | Japan | G01N 27/30 |
| 1-114746 | 5/1989 | Japan | G01N 27/46 |
| 1-114747 | 5/1989 | Japan | G01N 27/46 |
| 1-156658 | 6/1989 | Japan | G01N 27/46 |
| 2154003 | 2/1988 | United Kingdom | G01N 27/28 |
| 2204408 | 11/1988 | United Kingdom | G01N 27/12 |
| WO89/08713 | 9/1989 | WIPO | G01N 27/26 |

OTHER PUBLICATIONS

Talbott, Jonathan Lee, "Enzymatic Amperometry of Glucose", a Ph.D. Dissertation for The Pennsylvania State University, Graduate School Department of Chemistry, dated Jan. 1988.

Nankai, et al., Japanese Sensor Newsletter, vol. 3, No. 1, Mar./1989—p.p. 16–20, published by Edison Sensor Technology Center, Case Western Reserve University, Cleveland, Ohio.

Williams et al, "Electrochemical–Enzymatic Analysis of Blood Glucose and Lactate", 1970, vol. 42, No. pp. 118–121, Analytical Chemistry.

*Primary Examiner*—William H. Beisner
*Attorney, Agent, or Firm*—D. Michael Young; Max J. Kenemore; Marilyn L. Amick

[57] ABSTRACT

A new electrochemical biosensor and method of its use. The electrochemical biosensor has a pair of electrodes consisting of a working electrode and a counter electrode made of the same electrically conducting materials. The counter electrode may be the same size or smaller than the working electrode. The biosensor includes a sample receiving portion wherein a portion of the electrode surfaces is covered by a reagent that includes a redox mediator and an enzyme. A fluid that contains an analyte is added to the sample receiving portion. A reaction involving the analyte, enzyme and redox mediator occurs. After this reaction is complete, an electrical potential difference is applied between the electrodes. Diffusion limited current is measured and correlated to the concentration of analyte in the fluid.

20 Claims, 3 Drawing Sheets

ASSAY METHOD WITH ENZYME ELECTRODE SYSTEM

CROSS-REFERENCE TO RELATED APPLICATIONS

This application is a continuation-in-part of U.S. patent application Ser. No. 07/627,667, filed Dec. 14, 1990, now U.S. Pat. No. 5,288,636 issued Feb. 22, 1994, which is a continuation-in-part of U.S. patent application Ser. No. 07/451,671, filed Dec. 15, 1989, previously abandoned.

FIELD OF THE INVENTION

This invention relates generally to the determination of the concentration of analytes in fluids and more specifically to an amperometric biosensor for use in such determinations.

BACKGROUND OF THE INVENTION

Biosensors are not new. Their use in the determination of concentrations of various analytes in fluids is also known.

Nankai et al., WO 86/07632, published Dec. 31, 1986, discloses an amperometric biosensor system in which a fluid containing glucose is contacted with glucose oxidase and potassium ferricyanide. The glucose is oxidized and the ferricyanide is reduced to ferrocyanide. (This reaction is catalyzed by glucose oxidase.) After two minutes, an electrical potential is applied and a current caused by the re-oxidation of the ferrocyanide to ferricyanide is obtained. The current value, obtained a few seconds after the potential is applied, correlates to the concentration of glucose in the fluid.

Because Nankai et al. discloses a method in which the reaction of glucose and ferricyanide may run to completion prior to the application of an electrical potential, this method is referred to as the "end-point" method of amperometric determination.

Nankai et al. discloses a system, wherein the glucose oxidase and potassium ferricyanide are held on a non-woven nylon mesh. The mesh is positioned so that it is in contact with a working electrode, a counter electrode and a reference electrode. The total surface area of the counter and reference electrodes is twice that of the working electrode.

Wogoman, EP 0 206 218, published Dec. 30, 1986, discloses a biosensor having two electrodes, the electrodes being made of different electrically conducting materials. For example, the anode is formed from an anode material, such as platinum, and the cathode is formed from a cathode material, such as silver. The anode is coated with an enzyme. In a preferred embodiment, the coated electrode is covered with an elastomer that is permeable to glucose.

Pottgen et al., WO 89/08713, published Sep. 21, 1989, discloses the use of a two electrode biosensor, wherein the electrodes are made of the same noble metal, but one of the electrodes (referred to as a pseudo-reference electrode) is larger than the other (working) electrode.

Conventional wisdom in the electrochemical arts suggests biosensors of the following types:

1) a three electrode system, wherein a working electrode is referenced against a reference electrode (such as silver/silver chloride) and a counter electrode provides a means for current flow;

2) a two electrode system, wherein the working and counter electrodes are made of different electrically conducting materials; and 3) a two electrode system, wherein the working and counter electrodes are made of the same electrically conducting materials, but the counter electrode is larger than the working electrode.

Conventional wisdom in the electrochemical arts does not suggest that a biosensor could include a two electrode system, wherein the working and counter electrodes are substantially the same size (or wherein the counter electrode is smaller than the working electrode) and made of the same electrically conducting material.

SUMMARY OF THE INVENTION

The invention is a new biosensor (an electrochemical device) and method of its use. The biosensor includes working and counter electrodes of substantially the same size, made of the same electrically conducting material, and affixed to a first electrical insulator. Overlaying the electrodes is a second electrical insulator that includes a cutout portion that exposes substantially equal surface areas of the working and counter electrodes.

A reagent is added to the cutout portion. The reagent substantially covers the exposed electrode surfaces in the cutout portion and includes a redox mediator, an enzyme and preferably a buffer.

When a sample containing an analyte is added to the reagent, the analyte, enzyme, and the redox mediator participate in a reaction, wherein the redox mediator is either reduced (receives at least one electron) or is oxidized (donates at least one electron). Usually, in this reaction, the analyte is oxidized and the redox mediator is reduced. After this reaction (wherein analyte is oxidized and redox mediator is reduced) is complete, an electrical potential difference is applied between the electrodes. The amount of oxidized form of the redox mediator at the counter electrode and the applied potential difference must be sufficient to cause diffusion limited electrooxidation of the reduced form of the redox mediator at the surface of the working electrode. After a short time delay, current produced by the electrooxidation of the reduced form of the redox mediator is measured and the observed current is correlated to the amount of the analyte in the sample.

Importantly, only two electrodes of substantially the same size and made of the same electrically conducting material are required when the reagent includes a sufficient amount of the oxidized form of the redox mediator to insure that the current produced during electrooxidation is limited by the oxidation of the reduced form of the redox mediator at the working electrode surface.

For current produced during electrooxidation to be limited by the oxidation of the reduced form of the redox mediator at the working electrode surface, the amount of oxidized form of the redox mediator at the surface of the counter electrode must always exceed the amount of reduced form of the redox mediator at the surface to the working electrode.

DESCRIPTION OF THE INVENTION

Figure 1:
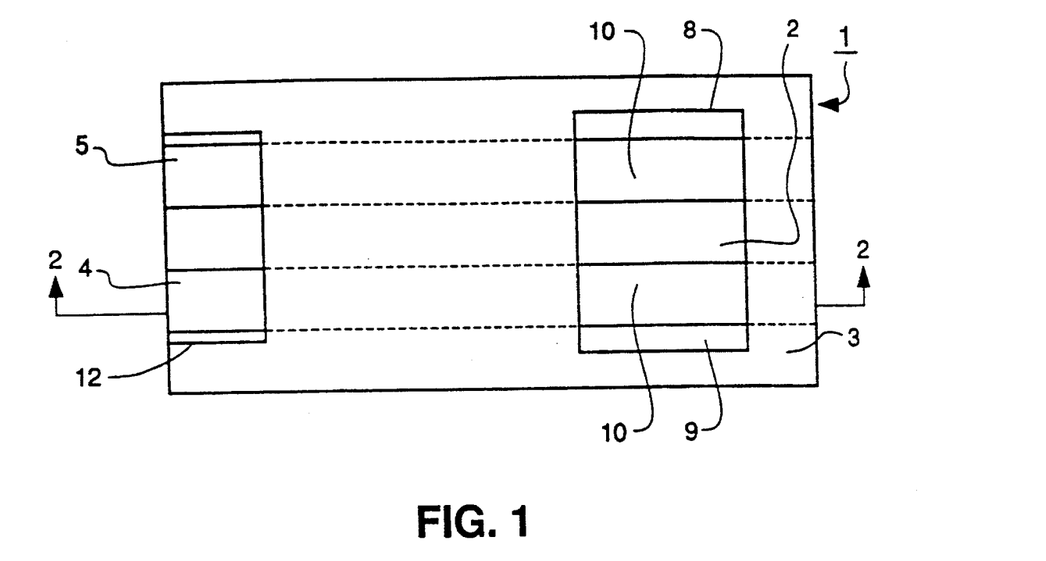
FIG. 1 is a schematic top view of a preferred embodiment of the inventive biosensor, excluding reagent and mesh covering.
Figure 2:
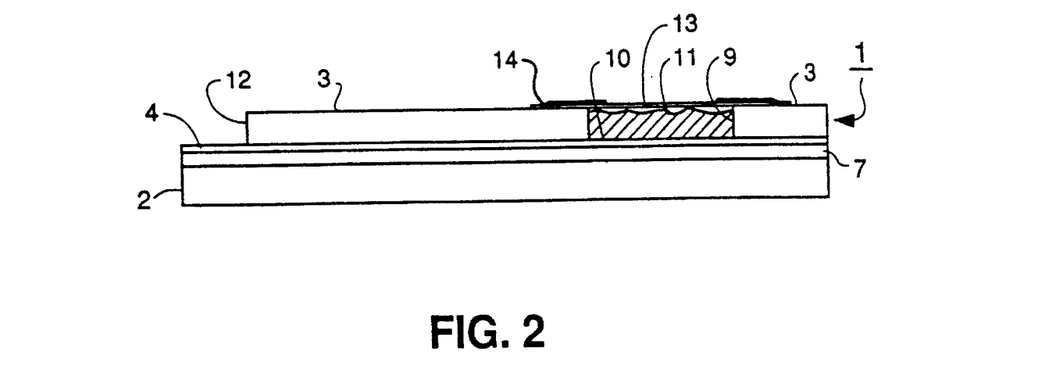
FIG. 2 is a schematic elevation of the inventive biosensor of FIG. 1 along lines 2—2, and including reagent and mesh covering.
Figure 3:
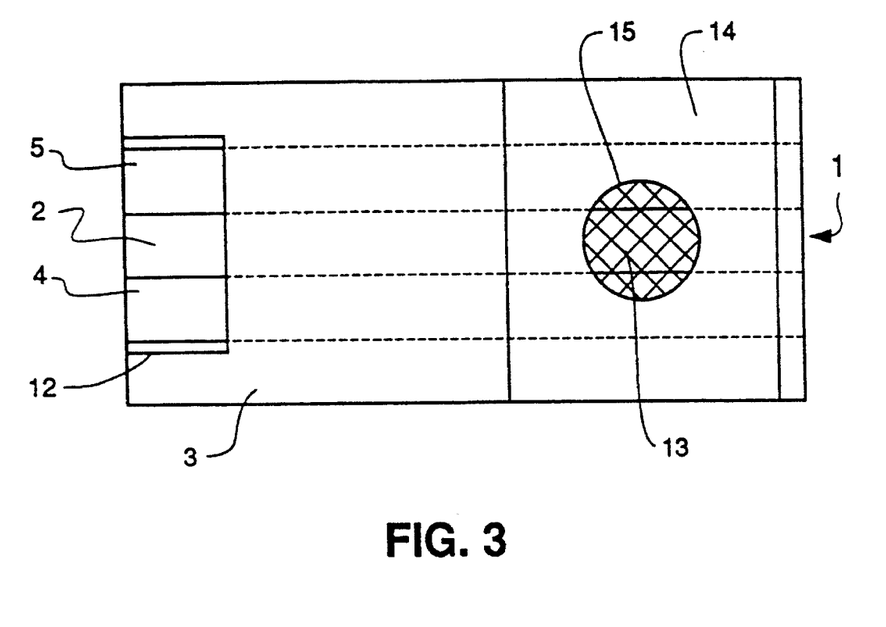
FIG. 3 is a schematic top view of a preferred embodiment of the inventive biosensor, including mesh covering.

Referring more specifically to FIGS. 1 through 3, there is shown the presently preferred embodiment of the biosensor of the present invention.

Biosensor 1 comprises first and second electrically insulating layers 2 and 3, respectively. Any useful insulating material will be suitable. Typically, plastics, such as vinyl polymers and polyimides provide the electrical and structural properties which are desired.

The biosensor shown in FIGS. 1 through 3 is intended to be mass produced from rolls of material, necessitating the selection of a material which is sufficiently flexible for roll processing and at the same time sufficiently stiff to give a useful stiffness to the finished biosensor.

Layers 2 and 3 may be of any useful thickness. In a preferred embodiment, layer 2 is about 360 microns thick and layer 3 is about 250 microns thick.

Working electrode 4 and counter electrode 5 are preferably deposited on a backing of insulator material 7, such as polyimide, to reduce the possibility of tearing the electrode before it is affixed to layer 2. Working electrode 4 and counter electrode 5 are substantially the same size and are made of the same electrically conducting material. Examples of electrically conducting materials that may be used are palladium, platinum, gold, silver, carbon, titanium, and copper. Noble metals are preferred because they provide a more constant, reproducible electrode surface area. Palladium is particularly preferred because it is one of the more difficult noble metals to oxidize and because it is a relatively inexpensive noble metal. Silver is not preferred because it is more readily oxidized by air than the other noble metals listed above. Preferably, electrodes 4 and 5 are about 0.1 micron thick and backing 7 is about 25 microns thick (commercially available from Courtalls-Andus Performance Films in California and Southwall Technologies, Inc.) (FIG. 2).

Electrodes 4 and 5 must be sufficiently separated so that the electrochemical events at one electrode do not interfere with the electrochemical events at the other electrode. The preferred distance between electrodes 4 and 5 is about 1.2 millimeters In the preferred embodiment, electrodes 4 and 5, affixed to backing 7, are unspooled from reels and attached to layer 2 by the use of hot melt adhesive (not shown). Electrodes 4 and 5 also preferably extend from one end of layer 2 to the other end in parallel configuration. (FIG. 1).

Insulating layer 3 is fixed on top of layer 2 and electrodes 4 and 5 by the use of hot melt adhesive (not shown). Layer 3 includes cut out portion 8, which defines reagent well 9 and exposes substantially equal surface areas 10 of electrodes 4 and 5.

In the preferred embodiment, cutout 8 is 4 mm by 6 mm and electrodes 4 and 5 are each 1.5 mm in width. Therefore, a surface area of about 6 mm² is exposed for each of the two electrodes.

Biosensor 1 also includes a power source (not shown) in electrical connection with the working and counter electrodes and a current measuring meter (not shown) which is also in electrical connection with the working and counter electrodes.

Biosensor reagent 11 (FIG. 2) is placed in well 9 so that it covers substantially all of exposed surfaces 10 of electrodes 4 and 5 and preferably covers the exposed surface of layer 2 between the electrodes.

At a minimum, reagent 11 includes the oxidized form of a redox mediator and an enzyme. Reagent 11 also preferably includes a buffer. The oxidized form of the redox mediator must be of sufficient type to receive at least one electron from a reaction involving enzyme, analyte, and oxidized form of the redox mediator. (The term redox mediator means a mediator that is capable of undergoing an electrochemical, reversible oxidation-reduction reaction.) The enzyme must be of sufficient type and in sufficient amount to catalyze the reaction involving enzyme, analyte and oxidized form of the redox mediator. If present, the buffer must be of sufficient type and in sufficient amount to provide and maintain a pH where the enzyme catalyzes the reaction involving enzyme, analyte and oxidized form of the redox mediator.

Generally, when a sample containing the analyte is added to the reagent, the analyte is oxidized and the oxidized form of the redox mediator is reduced as shown below:

The reaction shown above is permitted to go to completion. (Completion is defined as sufficient reaction involving analyte, enzyme, and redox mediator (oxidized form) to correlate analyte concentration to diffusion limited current generated by oxidation of the reduced form of the redox mediator at the surface of the working electrode.) After reaction is complete, a power source (e.g., a battery) applies a potential difference between the electrodes. When the potential difference is applied, the amount of oxidized form of the redox mediator at the counter electrode and the potential difference must be sufficient to cause diffusion limited electrooxidation of the reduced form of the redox mediator at the working electrode surface. The diffusion limited current generated by the oxidation of the reduced form of the redox mediator at the working electrode surface is measured by a current measuring meter.

The measured current may be accurately correlated to the concentration of analyte in the sample when the following requirements are satisfied:

1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

In the present inventive device, these requirements are satisfied by employing a readily reversible redox mediator and by supplying reagent 11 with the oxidized form of the redox mediator in an amount sufficient to insure that the current produced during diffusion limited electrooxidation is limited by the oxidation of the reduced form of the redox mediator at the working electrode surface. For current produced during electrooxidation to be limited by the oxidation of the reduced form of the redox mediator at the working electrode surface, the amount of oxidized form of the redox mediator at the surface of the counter electrode must always exceed the amount of the reduced form of the redox mediator at the surface of the working electrode.

Importantly, when the reagent includes an excess of the oxidized form of the redox mediator, as described below, the working and counter electrodes may be substantially the same size as well as made of the same electrically conducting material. The ability to utilize electrodes that are substantially the same size and made of the same material represents an important advantage for manufacturing a biosensor.

A further requirement of the reagent is that when a buffer is employed, the buffer must have a higher oxidation potential than the reduced form of the redox mediator.

The type of enzyme used will depend upon the analyte to be measured. For example, if glucose is the analyte to be measured, glucose oxidase may be used as the enzyme. If cholesterol is the analyte to be measured, cholesterol oxidase may be used as the enzyme.

As explained above, the redox mediator must be readily reversible and the oxidized form of the redox mediator must be of sufficient type to receive at least one electron from the reaction involving enzyme, analyte, and oxidized form of the redox mediator. For example, when glucose is the analyte to be measured and glucose oxidase is the enzyme, ferrocyanide or quinone may be the oxidized form of the redox mediator.

Other examples of enzymes and redox mediators (oxidized form) that may be used in measuring particular analytes by the present invention are listed below in Table 1.

In some of the examples shown in Table 1, at least one additional enzyme is used as a reaction catalyst. Also, some of the examples shown in Table 1 may utilize an additional mediator, which facilitates electron transfer to the oxidized form of the redox mediator. The additional mediator may be provided to the reagent in lesser amount than the oxidized form of the redox mediator.

The amount of enzyme included in the reagent may vary depending upon the time period desired for completion of the reaction involving analyte, enzyme, and oxidized form of the redox mediator. The more enzyme added, the shorter the time period for completion of the reaction. When a glucose reagent includes glucose oxidase, more than about 0.5 million o-dianisidine units (hereinafter units) of glucose oxidase per liter of reagent (referring to the reagent composition before being dried on the electrode surfaces) should be used in the reagent, and preferably about 2 million units of glucose oxidase per liter of reagent is used. Below about 0.5 million units per liter of reagent, assay performance is poor. About 2 million units of glucose oxidase per liter of reagent provides a reagent that will achieve completion of the reaction involving glucose, glucose oxidase, and ferricyanide within about 20 seconds, a conveniently short time period for the reaction. Above about 2 million units of glucose oxidase per liter of reagent, the reagent is needlessly more expensive to produce. (These amounts of glucose oxidase refer to the reagent composition before it is dried onto the electrode surfaces.)

The actual amount of oxidized form of the redox mediator needed in the reagent is governed by the concentration range of the analyte sought to be measured. The reagent for analyzing glucose (described herein) includes sufficient redox mediator (oxidized form) to measure the glucose level in a sample of human whole blood from about 10 to about 70 microliters (μl) in volume. The reagent must be provided with enough of the oxidized form of the redox mediator so that when the potential difference is applied between electrodes 4 and 5, the amount of oxidized form of the redox mediator at the surface of the counter electrode exceeds the amount of reduced form of the redox mediator at the working electrode.

TABLE I

| ANALYTE | ENZYMES | REDOX MEDIATOR OXIDIZED FORM) | ADDITIONAL MEDIATOR |
|---|---|---|---|
| GLUCOSE | GLUCOSE DEHYDROGENASE AND DIAPHOPASE | FERRICYANIDE | |
| CHOLESTEROL | CHOLESTEROL ESTERASE AND CHOLESTEROL OXIDASE | FERRICYANIDE | 2,6-DIMETHYL-1,4-BENZOQUINONE 2,5-DICHLORO-1,4-BENZOQUINONE OR PHENAZINE ETHOSULFATE |
| HDL CHOLESTEROL | CHOLESTEROL ESTERASE AND CHOLESTEROL OXIDASE | FERRICYANIDE 2,5-DICHLORO-1,4-BENZO-QUINONE | 2,6-DIMETHYL-1,4-BENZOQUINONE OR PHENAZINE ETHOSULFATE |
| TRIGLYC-ERIDES | LIPOPROTEIN LIPASE, GLYCEROL KINASE, AND GLYCEROL-3-PHOSPHATE OXIDASE | FERRICYANIDE OR PHENAZINE ETHOSULFATE | PHENAZINE METHOSULFATE |
| LACTATE | LACTATE OXIDASE | FERRICYANIDE, | 2,6-DICHLORO-1,4-BENZOQUINONE |
| LACTATE | LACTATE DEHYDROGENASE AND DIAPHORASE | FERIUCYANIDE, PHENAZINE ETHOSULFATE, OR PHENAZINE METHOSULPATE | |
| LACTATE DEHYDRO-GENASE | DIAPHORASE | FERRICYANIDE, PHENAZINE ETHOSULFATE, OR PHENAZINE METHOSULFATE | |
| PYRUVATE | PYRUVATE OXIDASE | FERRICYANIDE | |
| ALCOHOL | ALCOHOL OXIDASE | PHENYLENEDIAMINE | |
| BILIRUBIN | BILIRURIN OXIDASE | [-METHOXY-PHENAZINE METHOSULFATE | |
| URIC ACID | URICASE | FERRICYANIDE | |

The upper limit of the amount of redox mediator (oxidized form) will usually depend on the mediator's solubility and dispersion properties in the reagent. The reagent for the present invention, exemplified by a biosensor for the assay of glucose, preferably includes a microcrystalline material of sufficient type and in sufficient amount to disperse the redox mediator in the reagent.

Examples of microcrystalline materials that will disperse the redox mediator are microcrystalline cellulose, dextrans, and chitin. The amount of microcrystalline material included in the preferred glucose reagent, which includes glucose oxidase and potassium ferricyanide, is from about 1% (weight:volume) to about 4.5% (weight:volume), and is preferably about 1.5% (weight:volume). Below about 1% (weight:volume) microcrystalline material, the reagent will fall off of the electrode surfaces after drying. Above about 4.5% (weight:volume) microcrystalline material, the reagent gels. For a glucose reagent that includes ferricyanide and glucose oxidase, the preferred microcrystalline material is a combination of AVICEL RC-591 F (a microcrystalline cellulose available from FMC Corp.) and NATROSOL-250 M (a microcrystalline hydroxyethylcellulose available from Aqualon). The amount of AVICEL in the reagent may range from about 1% to about 4.2% (weight:volume) and is preferably about 1.4% (weight:volume). The amount of NATROSOL in the reagent may range from about 0% to about 0.3% (weight:volume) and is preferably about 0.06% (weight:volume). (These percentages refer to the reagent composition before it is dried onto the electrode surfaces.)

When AVICEL and NATROSOL are added to the reagent, in the ranges stated above, the amount of potassium ferricyanide that may be incorporated into the reagent may range from about 0.15 molar (M) to about 0.7M, and is preferably about 0.3M. When the concentration of ferricyanide is below about 0.15M and above about 0.7M, performance of the biosensor decreases. (These molarities refer to the reagent composition before it is dried onto the electrode surfaces.)

The reagent also preferably includes a surfactant of sufficient type and in sufficient amount to wet a sample containing the analyte to be measured. For example, in a reagent for analyzing a sample of human whole blood containing glucose, the surfactant is preferably a nonionic surfactant. From about 0% (weight:volume) to about 0.3% (weight:volume) surfactant may be present in the reagent. Above about 0.3% (weight:volume) surfactant, red blood cells begin to hemolyze. The preferred surfactant in the glucose reagent is TRITON X-100 (available from Sigma Chemical Corporation) at a preferred concentration of about 0.05% (weight:volume). (Percentages refer to the reagent composition before it is dried onto the electrode surfaces.)

Any buffer that satisfies the above-stated requirements of providing a satisfactory pH for enzyme function and having a higher oxidation potential than the reduced form of the redox mediator may be used.

Examples of such buffers for a glucose reagent utilizing the enzyme glucose oxidase include phosphate, citrate (citrate also helps stabilize the reagent), "Good" buffers (e.g., 2-(N-morpholino) ethanesulfonic acid, N-(2-acetamido)-2-iminodiacetic acid, piperazine-N,N'-bis (2-ethanesulfonic acid), N-(2-acetamido)-2-aminoethanesulfonic acid, N,N-bis (2-hydroxyethyl)-2-aminoethanesulfonic acid, N-tris (hydroxymethyl) methyl-2-aminoethanesulfonic acid, and N-2-hydroxyethylpiperazine-N'-2-ethanesulfonic acid, and Tris buffers (buffers derived from 2-amino-2(hydroxymethyl)-1,3-propanediol). ("Good" and Tris buffers are available from Sigma Chemical Company.) Imidazole should not be used as a buffer. These buffers may be used to provide a preferred pH range from about 4 to about 8. The most preferred pH range is from about 6 to about 7. The most preferred buffer is phosphate (e.g., potassium phosphate) from about 0.1M to about 0.5M and preferably about 0.4M. (These concentration ranges refer to the reagent composition before it is dried onto the electrode surfaces.)

The reagent preferably further includes a reagent stabilizer of sufficient type and in sufficient amount to stabilize the reagent. The reagent stabilizer stabilizes the enzyme, and for a glucose reagent containing glucose oxidase, the reagent stabilizer may be glutamate, succinate, aspartate, blue dextran or trehalose. A preferred reagent stabilizer for a reagent containing glucose oxidase is glutamate (e.g., potassium glutamate) at a concentration range from about 0% (weight:volume) to about 4% (weight:volume), with the preferred amount being about 2% (weight:volume). A more preferred reagent stabilizer for a reagent containing glucose oxidase is succinate at a concentration of about 1% (weight:volume). (These percentages refer to the reagent composition before it is dried onto the electrode surfaces.)

A protocol for making a glucose reagent utilizing the enzyme glucose oxidase and ferricyanide as the oxidized form of the redox mediator is as follows:

Step 1—Prepare 1 liter (in a volumetric flask) of a buffer/NATROSOL mixture by adding 1.2000 grams (g) NATROSOL-250 M to 0.740M aqueous potassium phosphate buffer (including 80.062 g monobasic potassium phosphate and 26.423 g dibasic potassium phosphate) at pH 6.25. Allow the NATROSOL to stir and swell for 3 hours.

Step 2—Prepare an AVICEL mixture by stirring 14.0000 g AVICEL RC-591 F and 504.7750 g water for 20 minutes.

Step 3—Prepare a TRITON mixture by adding 0.5000 g TRITON X-100 to 514.6000 g of the buffer/NATROSOL mixture and stir for 15 minutes.

Step 4—While stirring, add the total TRITON mixture dropwise with a dropwise addition funnel or buret to the total AVICEL mixture. Once addition is complete, continue stirring overnight.

Step 5—To the mixture resulting from Step 4, add, while stirring, 98.7750 g potassium ferricyanide. (Add a little potassium ferricyanide at a time to allow the potassium ferricyanide to dissolve as added.)

Step 6—Stir the resulting mixture of Step 5 for 20 minutes.

Step 7—Adjust the pH of the mixture resulting from Step 6 to 6.25 by adding potassium hydroxide.

Step 8—To the resulting mixture of Step 7, add 9.1533 g glucose oxidase (218.50 units per milligram (mg) from Biozyme) and stir at least 20 minutes.

Step 9—To the resulting mixture of Step 8, add 20 g potassium glutamate and stir at least 20 minutes.

Step 10—Filter the resulting mixture of Step 9 through a 100 micron sieve bag to remove any AVICEL dumping. The filtrate is the resulting reagent composition, which is added to the electrode surfaces and is then dried.

In the preferred embodiment for glucose determination, 6 microliters (µl) of reagent made by the above-stated protocol is added to well 9 formed by cutout 8. This amount of reagent 11 will substantially cover surface areas 10 on both electrodes (FIGS. 1 and 2) and will also contain a sufficient amount of ferricyanide, and a sufficient amount of enzyme (glucose oxidase) to catalyze the oxidation of glucose (from a sample of human whole blood) and the reduction of ferricyanide to completion within about 20 seconds. (Prior to adding the reagent to well 9, it is preferable to treat well 9 with a 600 Watt corona arc, gapped at 1/40,000 inch on a processing line travelling at 4 meters per minute, to make well 9 more hydrophilic, thereby allowing the reagent to spread more evenly in the well.)

Reagent 11 is then dried by heating at about 50° C. for about 3 minutes. Drying removes at least about 90% of the water content of the reagent, thereby resulting in a preferred dried reagent with the following proportions of components: from about 1.1 to about 1.5 millimoles (mmol) ferricyanide per gram of dried reagent; from about 2,300 to about 2,600 units of glucose oxidase per gram of dried reagent, assuming 75% loss of enzyme activity (an unusually high loss of enzyme activity) from reagent drying, from about 8,600 to about 9,600 units of glucose oxidase per gram of dried reagent, assuming a more typical 6% loss of enzyme activity from reagent drying, and from about 9,200 to about 10,400 units of glucose oxidase per gram of dried reagent, assuming no loss of enzyme activity from reagent drying; from about 1.3 to about 1.9 m mol phosphate buffer per gram of dried reagent; from about 2 to about 3 milligrams (mg) NATROSOL-250 M per gram of dried reagent and from about 50 to about 71 mg AVICEL RC-591 F per gram of dried reagent (a total of from about 52 to about 74 mg microcrystalline material per gram of dried reagent); from about 71 to about 102 mg glutamate per gram of dried reagent; and from about 2 to about 3 mg TRITON X-100 per gram of dried reagent.

As stated above, each component of the formulated reagent (before drying) may vary within the disclosed limits. Therefore, a glucose reagent dried as above may include the following broader ranges of components: from about 0.55 to about 3.5 m mol ferricyanide per gram of dried reagent; more than about 570 units of glucose oxidase per gram of dried reagent, assuming a 75% loss of enzyme activity (an unusually high loss of enzyme activity) from reagent drying, and more than about 2100 units of glucose oxidase per gram of dried reagent, assuming a more typical 6% loss of enzyme activity from reagent drying; from about 0.35 to about 2.6 m mol phosphate per gram of dried reagent; from about 0 to about 15 mg NATROSOL-250 M per gram of dried reagent and from about 36 to about 213 mg AVICEL RC-591 F per gram of dried reagent (a total of from about 36 to about 228 mg microcrystalline material per gram of dried reagent); from about 0 to about 200 mg glutamate per gram of dried reagent; and from about 0 to about 18 mg TRITON X-100 per gram of dried reagent.

Another glucose reagent that may be formulated includes 300 millimolar potassium ferricyanide, 250 millimolar potassium phosphate buffer, 14 grams microcrystalline cellulose (AVICEL RC-591 F) per liter of reagent, 0.6 grams hydroxyethylcellulose (NATROSOL-250 M) per liter of reagent, 0.5 grams Triton X-100 surfactant per liter of reagent, 37 millimolar sodium succinate, and 1.57 million tetramethyl benzidine units of glucose oxidase per liter of reagent. Sodium hydroxide (6 Normal solution) is used to titrate this reagent to a pH of 6.6. This reagent may be formulated by the same protocol described above, but amounts of components should be adjusted and components substituted (sodium succinate for potassium glutamate and sodium hydroxide for potassium hydroxide) to achieve the component concentrations stated above.

After drying reagent 11, a polyester or nylon mesh 13 (FIGS. 2 and 3) is preferably placed on top of the dried reagent to aid in preventing loss of reagent from the biosensor during shipping and handling and to aid in minimizing human contamination from the reagent. (The mesh is preferably dipped in a solution of 0.7% (weight:volume) dioctylsodium sulfosuccinate (DONS) in methanol and then dried.) Mesh 13 is affixed to the inventive device by adhesive tape 14, which includes hole 15. (FIGS. 2 and 3) Hole 15 is the target area for adding a sample containing an analyte to be measured by the inventive device. (FIG. 3) (Preferably, hole 15 is slightly offset from the centerline between electrodes 4 and 5 so that more of working electrode 4 is exposed through hole 15 than counter electrode 5, thereby aiding in the complete wetting of the reagent coveting the working electrode when small volumes of sample fluid are tested by the device.)

After drying the reagent and affixing the mesh, the roll-formed biosensors are separated by die punching to form discrete biosensors, which are used in conjunction with 1) a power source in electrical connection with the working and counter electrodes and capable of supplying an electrical potential difference between the working and counter electrodes sufficient to cause diffusion limited electrooxidation of the reduced form of the redox mediator at the surface of the working electrode, and 2) a meter in electrical connection with the working and counter electrodes and capable of measuring the diffusion limited current produced by oxidation of the reduced form of the redox mediator when the above-stated electrical potential difference is applied.

The meter described above will normally be adapted to apply an algorithm (discussed below) to the current measurement, whereby an analyte concentration is provided and visually displayed. Improvements in such a power source, meter, and biosensor system are the subject of commonly assigned U.S. Pat. No. 4,963,814, issued Oct. 16, 1990, U.S. Pat. No. 4,999,632, issued Mar. 12, 1991, U.S. Pat. No. 4,999,582, issued Mar. 12, 1991, and U.S. Pat. No. 5,243,516, issued Sep. 7, 1993, the disclosures of which are hereby incorporated by reference.

For easy electrical connection of the power source and meter, additional cutout portion 12 (FIGS. 1 through 3), exposing portions of the working and counter electrodes, are preferably provided in the biosensor device.

The biosensor device described above may be used to determine the concentration of an analyte in a fluid sample by performing the following steps:

a) contacting the fluid sample with a reagent (described above) that substantially covers substantially equal surface areas of working and counter electrodes;

b) allowing the reaction between the analyte and the oxidized form of the redox mediator to go to completion;

c) subsequently applying a potential difference between the electrodes sufficient to cause diffusion limited electrooxidation of the reduced form of the redox mediator at the surface of the working electrode;

d) thereafter measuring the resulting diffusion limited current; and e) correlating the current measurement to the concentration of analyte in the fluid.

Many analyte-containing fluids may be analyzed. For example, analytes in human body fluids such as whole blood, blood serum, urine and cerebrospinal fluid may be measured. Also, analytes found in fermentation products and in environmental substances, which potentially contain environmental contaminants, may be measured.

When measuring analytes found in human body fluids, especially whole blood, the potential difference applied between the electrodes should be no more than about 500 millivolts. When a potential difference above about 500 millivolts is applied between the electrodes, oxidation of the working electrode surface (for palladium) and of some blood components can become intolerable, thereby preventing an accurate and precise correlation of current to analyte concentration. For an assay of glucose in a whole blood sample, wherein the oxidized form of the redox mediator is ferricyanide, a potential difference from about 150 millivolts to about 500 millivolts may be applied between the electrodes to achieve diffusion limited electrooxidation of the reduced form of the redox mediator at the surface of the working electrode. Preferably, about 300 millivolts potential difference is applied between the electrodes.

Current generated from the oxidation of the reduced form of the redox mediator may be measured at any time from about 0.5 seconds to about 30 seconds after the potential difference is applied between the electrodes. At less than about 0.5 seconds, diffusion limited current has not been achieved. After about 30 seconds, convection becomes significant, thereby interfering with the measurement of a diffusion limited current.

Figure 4:
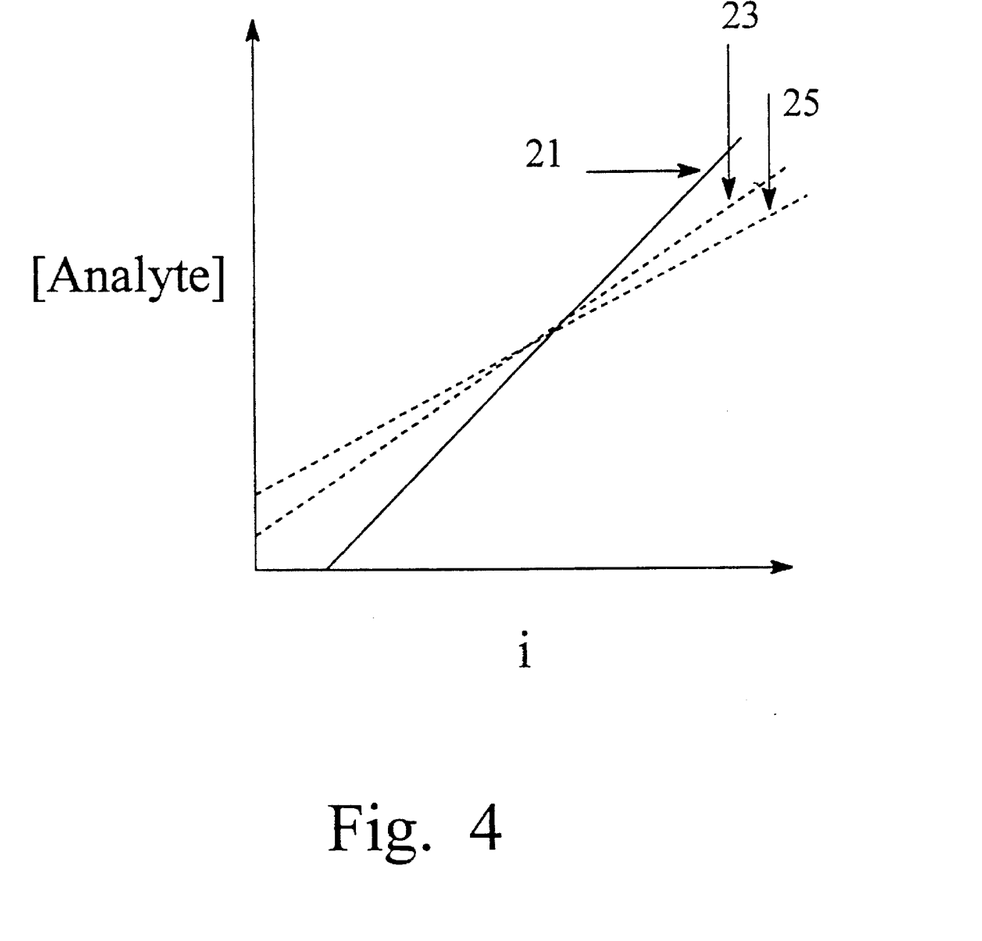
FIG. 4 illustrates hypothetical calibration curves for different lots of biosensors.

The current measured during the assay of an analyte from a fluid sample may be correlated to concentration of the analyte in the sample by application of an algorithm by the current measuring meter. The algorithm may be a simple one, as illustrated by the following example:

$$[\text{Analyte}] = Ci_{7.5} + d$$

wherein [Analyte] represents the concentration of the analyte in the sample (see FIG. 4), $i_{7.5}$ is the current (in microamps) measured at 7.5 seconds after application of the potential difference applied between the electrodes, C is the slope of line 21 (FIG. 4), and d is the axis intercept (FIG. 4).

By making measurements with known concentrations of analyte, calibration curve 21 (FIG. 4) may be constructed. This calibration will be stored in the Read Only Memory (ROM) key of the meter and will be applicable to a particular lot of biosensors. Lines 23 and 25 in FIG. 4 represent other hypothetical calibration curves for two other different lots of biosensors. Calibration for these biosensor lots would generate slightly different values for C and d in the above algorithm.

In the preferred method for analysis of glucose from a sample of human whole blood, 20 μl of whole blood is added to the above-stated preferred glucose reagent. The reaction of glucose and ferricyanide is allowed to go to completion, thereby forming gluconic acid and ferrocyanide. This reaction normally requires a short time to go to completion, and in the preferred embodiment, the reaction goes to completion in less than about 20 seconds. About twenty seconds after addition of the whole blood sample, a potential difference of about 300 millivolts is applied between the electrodes, thereby oxidizing ferrocyanide to ferricyanide at the surface of the working electrode. Current measurements are made at 0.5 second intervals from 1 second to 7.5 seconds after the potential difference is applied between the electrodes. These current measurements are correlated to the concentration of glucose in the blood sample.

In this example of measuring glucose from a blood sample, current measurements are made at different times (from 1 second to 7.5 seconds after application of the potential difference), rather than at a single fixed time (as described above), and the resulting algorithm is more complex and may be represented by the following equation:

$[\text{Glucose}] = C_1 i_1 + C_2 i_2 + C_3 i_3 + \ldots C_n i_n + d$, wherein $i_1$ is the current measured at the first measurement time (1 second after application of the 300 millivolt potential difference), $i_2$ is the current measured at the second measurement time (1.5 seconds after application of the 300 millivolt potential difference), $i_3$ is the current measured at the third measurement time (2 seconds after application of the 300 millivolt potential difference), $i_n$ is the current measured at the $n^{th}$ measurement time (in this example, at the $14^{th}$ measurement time or 7.5 seconds after application of the 300 millivolt potential difference), $C_1$, $C_2$, $C_3$, and $C_n$ are coefficients derived from a multivariate regression analysis technique, such as Principle Components Analysis or Partial Least Squares, and d is the regression intercept (in glucose concentration units).

Alternatively, the concentration of glucose in the sample being measured may be determined by integrating the curve generated by plotting current, i, versus measurement time over some time interval (for example, from 1 second to 7.5 seconds after application of the 300 millivolt potential difference), thereby obtaining the total charge transferred during the measurement period. The total charge transferred is directly proportional to the concentration of glucose in the sample being measured.

Further, the glucose concentration measurement may be corrected for differences between environmental temperature at the time of actual measurement and the environmental temperature at the time calibration was performed. For example, if the calibration curve for glucose measurement was constructed at an environmental temperature of 23° C., the glucose measurement is corrected by using the following equation:

$[\text{Glucose}]_{corrected} = [\text{Glucose}]_{measured} \times (1 - K(T - 23°\ \text{C.}))$, wherein T is the environmental temperature (in °C.) at the time of the sample measurement and K is a constant derived from the following regression equation:

$$Y = K(T-23),$$

wherein $$Y = \frac{[\text{Glucose}]_{measured\ at\ 23°\ C.} - [\text{Glucose}]_{measured\ at\ T°\ C.}}{[\text{Glucose}]_{measured\ at\ T°\ C.}}$$

In order to calculate the value of K, each of a multiplicity of glucose concentrations is measured by the meter at various temperatures, T, and at 23° C. (the base case). Next, a linear regression of Y on T-23 is performed. The value of K is the slope of this regression.

The glucose concentration of a sample may be accurately and precisely measured by the present inventive method utilizing the present inventive biosensor. Further, when a sample of human whole blood is measured, error due to hematocrit effect is insignificant in the range of 30–55% hematocrit.

As a variation of the present invention, the counter electrode could be smaller than the working electrode. When the counter electrode is smaller than the working electrode, the amount of oxidized form of the redox mediator supplied to reagent 11 must be increased. The amount of oxidized form of the redox mediator in reagent 11 must be increased because the above-stated requirements for accurately correlating concentration of the analyte to current must be satisfied; that is, 1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

For example, it has been shown that when the counter electrode is about half the size of the working electrode, a mixture of about 2700 nanomoles (nmol) of ferricyanide and about 900 nmol of ferrocyanide (dissolved in 20 μl of water) satisfied the requirements stated above.

Also, the present invention has been illustrated by analytes that are oxidized and redox mediators that are reduced in the presence of a catalytic amount of enzyme. However, the present inventive device, reagents and methods may also be used to measure the concentration of an analyte in a fluid sample, wherein the analyte is reduced and the reduced form of a redox mediator is oxidized in the presence of a catalytic amount of an enzyme (e.g., a reductase). After the reaction involving analyte, enzyme, and reduced form of the redox mediator reaches completion, a potential difference is applied between the electrodes. The amount of reduced form of the redox mediator at the counter electrode (in this case an anode rather than a cathode) and the applied potential difference must be sufficient to cause diffusion limited electroreduction of the oxidized form of the redox mediator at the surface of the working electrode (in this case a cathode rather than an anode). The diffusion limited current generated by reduction of the oxidized form of the redox mediator at the working electrode surface is correlated to the concentration of analyte in the sample being analyzed.

The redox mediator must be readily reversible and the amount of reduced form of the redox mediator in reagent 11 must be sufficient to insure that the current produced during electroreduction is limited by the reduction of the oxidized form of the redox mediator at the working electrode surface.

A buffer is preferably included and, if present, the buffer must have a lower reduction potential than the reduction potential of the oxidized form of the redox mediator and must be of sufficient type and in sufficient amount to provide and maintain a pH at which the enzyme catalyzes the reaction involving analyte, enzyme and the reduced form of the redox mediator. These requirements and other requirements are analogous to the requirements for measuring an analyte that is oxidized rather than reduced.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

We claim:

1. A method, practiced with an electrochemical cell having a pair of electrodes consisting of working and counter electrodes of substantially the same size, the electrodes being made of the same electrically conducting materials, for determining the concentration of an analyte in a fluid, comprising:

a. contacting the fluid with a reagent that covers substantially equal surface areas of working and counter electrodes in a sample receiving portion of the electrochemical cell, thereby exposing the entire reagent to the fluid, wherein the reagent includes the oxidized form of a redox mediator and an enzyme, the oxidized form of the redox mediator being of sufficient type to receive at least one electron from a reaction involving enzyme, analyte, and oxidized form of the redox mediator and being in sufficient amount to insure that current produced by diffusion limited electrooxidation is limited by the oxidation of the reduced form of the redox mediator at the working electrode surface, and the enzyme being of sufficient type and in sufficient amount to catalyze the reaction involving enzyme, analyte, and the oxidized form of the redox mediator;

b. allowing the reaction involving the enzyme, analyte, and the oxidized form of the redox mediator to go to completion;

c. subsequently applying a potential difference between the electrodes sufficient to cause diffusion limited electrooxidation of the reduced form of the redox mediator at the surface of the working electrode;

d. thereafter measuring the resulting diffusion limited current; and e. correlating the current measurement to the concentration of the analyte in the fluid.

2. The method of claim 1, wherein the reagent further includes a buffer having a higher oxidation potential than the reduced form of the redox mediator, the buffer being of sufficient type and in sufficient amount to provide and maintain a pH at which the enzyme catalyzes the reaction involving enzyme, analyte, and the oxidized form of the redox mediator.

3. The method of claim 2, wherein the reagent further includes at least one additional enzyme and an additional redox mediator.

4. The method of claim 2, wherein the reagent further includes a microcrystalline material of sufficient type and in sufficient amount to disperse the redox mediator in the reagent.

5. The method of claim 4, wherein the reagent further includes:

a surfactant of sufficient type and in sufficient amount to aid wetting of the reagent by the fluid, and a reagent stabilizer of sufficient type and in sufficient amount to stabilize the reagent.

6. The method of claim 5, wherein the analyte is glucose, the oxidized form of the redox mediator is ferricyanide, the buffer is phosphate, the microcrystalline material includes microcrystalline cellulose and microcrystalline hydroxyethylcellulose, the enzyme is glucose oxidase, the surfactant is a nonionic surfactant, and the reagent stabilizer is glutamate, succinate, aspartate, blue dextran, or trehalose.

7. The method of claim 6, wherein the reagent includes:

from about 1.1 to about 1.5 millimoles ferricyanide per gram of reagent, from about 1.3 to about 1.9 millimoles phosphate buffer per gram of reagent, from about 2,300 to about 10,400 units of glucose oxidase per gram of reagent, from about 50 to 71 milligrams microcrystalline cellulose per gram of reagent, from about 2 to about 3 milligrams microcrystalline hydroxyethylcellulose per gram of reagent, from about 2 to about 3 milligrams TRITON X-100 per gram of reagent, and from about 71 to about 102 milligrams glutamate per gram of reagent.

8. The method of claim 6, wherein the reagent includes, before drying, about 300 millimolar potassium ferricyanide, about 250 millimolar phosphate buffer, about 14 grams microcrystalline cellulose per liter of reagent, about 0–6 grams hydroxyethylcellulose per liter reagent, about 0.5 grams Triton X-100 surfactant per liter of reagent, about 37 millimolar succinate, and about 1.6 million tetramethyl benzidine units of glucose oxidase per liter of reagent, wherein the reagent pH is about 6.6.

9. A method, practiced with an electrochemical cell having a pair of electrodes consisting of working and counter electrodes of substantially the same size, the electrodes being made of the same electrically conducting materials, for determining the concentration of an analyte in a fluid, comprising:

a. contacting the fluid with a reagent that covers substantially equal surface areas of working and counter electrodes in a sample receiving portion of the electrochemical cell, thereby exposing the entire reagent to the fluid, wherein the reagent includes the reduced form of redox mediator and an enzyme,   the reduced form of the redox mediator being of sufficient type to donate at least one electron from a reaction involving enzyme, analyte, and reduced form of the redox mediator and being in sufficient amount to insure that current produced by diffusion limited electroreduction is limited by the reduction of the oxidized form of the redox mediator at the working electrode surface, and   the enzyme being of sufficient type and in sufficient amount to catalyze the reaction involving enzyme, analyte, and the reduced form of the redox mediator;

b. allowing the reaction involving the enzyme, analyte, and the reduced form of a redox mediator to go to completion;

c. subsequently applying a potential difference between the electrodes sufficient to cause diffusion limited electroreduction of the oxidized form of the redox mediator at the surface of the working electrode;

d. thereafter measuring the resulting diffusion limited current; and   e. correlating the current measurement to the concentration of the analyte in the fluid.

10. The method of claim 9, wherein the reagent further includes a buffer having lower reduction potential than the oxidized form of the redox mediator, the buffer being of sufficient type and in sufficient amount to provide and maintain a pH at which the enzyme catalyzes the reaction involving enzyme, analyte, and the reduced form of the redox mediator.

11. The method of claim 10, wherein the reagent further includes:

a microcrystalline material of sufficient type and in sufficient amount to disperse the redox mediator in the reagent,   a surfactant of sufficient type and in sufficient amount to wet a sample containing the analyte, and   a reagent stabilizer of sufficient type and in sufficient amount to stabilize the reagent.

12. A method, practiced with an electrochemical cell having a pair of electrodes consisting of a working electrode and a counter electrode that is smaller than the work,ha electrode, the electrodes being made of the same electrically conducting materials, of determining the concentration of an analyte in a fluid, comprising:

a. contacting the fluid with a reagent that covers a smaller surface area of the counter electrode than the working electrode in a sample receiving portion of the electrochemical cell, thereby exposing the entire reagent to the fluid wherein the reagent includes the oxidized form of a redox mediator and an enzyme,   the oxidized form of the redox mediator being of sufficient type to receive at least one electron from a reaction involving enzyme, analyte, and oxidized form of the redox mediator and being in sufficient amount to insure that current produced by diffusion limited electrooxidation is limited by the oxidation of the reduced form of the redox mediator at the working electrode surface, and   the enzyme being of sufficient type and in sufficient amount to catalyze the reaction involving enzyme, analyte, and the oxidized form of the redox mediator;

b. allowing the reaction involving the enzyme, analyte, and the oxidized form of the redox mediator to go to completion;

c. subsequently applying a potential difference between the electrodes sufficient to cause diffusion limited electrooxidation of the reduced form of the redox mediator at the surface of the working electrode;

d. thereafter measuring the resulting diffusion limited current; and   e. correlating the current measurement to the concentration of the analyte in the fluid.

13. The method of claim 12, wherein the reagent further includes a buffer having a higher oxidation potential than the reduced form of the redox mediator, the buffer being of sufficient type and in sufficient amount to provide and maintain a pH at which the enzyme catalyzes the reaction involving enzyme, analyte, and the oxidized form of the redox mediator.

14. The method of claim 13, wherein the reagent further includes at least one additional enzyme and an additional redox mediator.

15. The method of claim 13, wherein the reagent further includes a microcrystalline material of sufficient type and in sufficient amount to disperse the redox mediator in the reagent.

16. The method of claim 15, wherein the reagent further includes:

a surfactant of sufficient type and in sufficient amount to aid wetting of the reagent by the fluid, and   a reagent stabilizer of sufficient type and in sufficient amount to stabilize the reagent.

17. The method of claim 16, wherein the analyte is glucose, the oxidized form of the redox mediator is ferricyanide, the buffer is phosphate, the microcrystalline material includes microcrystalline cellulose and microcrystalline hydroxyethylcellulose, the enzyme is glucose oxidase, the surfactant is a nonionic surfactant, and the reagent stabilizer is glutamate, succinate, aspartate, blue dextran, or trehalose.

18. A method, practiced with an electrochemical cell having a pair of electrodes consisting of a working electrode and a counter electrode that is smaller than the working electrode, the electrodes being made of the same electrically conducting materials of determining the concentration of an analyte in a fluid, comprising:

a. contacting the fluid with a reagent that covers smaller surface area of the counter electrode than the working electrode in a sample receiving portion of the electrochemical cell, thereby exposing the entire reagent the fluid, wherein the reagent includes the reduced form of a redox mediator and an enzyme,   the reduced form of the redox mediator being of sufficient type to donate at least one electron from a reaction involving enzyme, analyte, and reduced form of the redox mediator and being in sufficient amount to insure that current produced by diffusion limited electroreduction is limited by the reduction of the oxidized form of the redox mediator at the working electrode surface, and   the enzyme being of sufficient type and in sufficient amount to catalyze the reaction involving enzyme, analyte, and the reduced form of the redox mediator;

b. allowing the reaction involving the enzyme, analyte, and the reduced form of the redox mediator to go to completion;

c. subsequently applying a potential difference between the electrodes sufficient to cause diffusion limited electroreduction of the oxidized form of the redox mediator at the surface of the working electrode;

d. thereafter measuring the resulting diffusion limited current; and e. correlating the current measurement to the concentration of the analyte in the fluid.

19. The method of claim 18, wherein the reagent further includes a buffer having lower reduction potential than the oxidized form of the redox mediator, the buffer being of sufficient type and in sufficient amount to provide and maintain a pH at which the enzyme catalyzes the reaction involving enzyme, analyte, and the reduced form of the redox mediator.

20. The method of claim 19, wherein the reagent further includes:

a microcrystalline material of sufficient type and in sufficient amount to disperse the redox mediator in the reagent, a surfactant of sufficient type and in sufficient amount to aid wetting of the reagent by the fluid, and a reagent stabilizer of sufficient type and in sufficient amount to stabilize the reagent.

* * * * *